(12) United States Patent
Ziglioli et al.

(10) Patent No.: US 8,499,613 B2
(45) Date of Patent: Aug. 6, 2013

(54) INTEGRATED CHEMICAL SENSOR FOR DETECTING ODOROUS MATTERS

(75) Inventors: Federico Giovanni Ziglioli, Pozzo D'Adda (IT); Amedeo Maierna, Albuzzano (IT); Flavio Francesco Villa, Milan (IT); Ubaldo Mastromatteo, Bareggio (IT); Gabriele Barlocchi, Cornaredo (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 258 days.

(21) Appl. No.: 13/016,086

(22) Filed: Jan. 28, 2011

(65) Prior Publication Data

US 2011/0209524 A1    Sep. 1, 2011

(30) Foreign Application Priority Data

Jan. 29, 2010   (IT) ................ TO2010A0067

(51) Int. Cl.
    *G01N 7/04*   (2006.01)
(52) U.S. Cl.
    USPC ........................................ 73/23.34
(58) Field of Classification Search
    USPC ........................................ 73/23.34
    See application file for complete search history.

(56) References Cited

U.S. PATENT DOCUMENTS

| | | | |
|---|---|---|---|
| 3,715,911 A * | 2/1973 | Chuan | 73/24.03 |
| 4,549,427 A * | 10/1985 | Kolesar, Jr. | 73/24.01 |
| 5,018,395 A | 5/1991 | Hickox et al. | |
| 5,469,369 A * | 11/1995 | Rose-Pehrsson et al. | 702/27 |
| 5,692,279 A | 12/1997 | Mang et al. | |
| 6,085,576 A | 7/2000 | Sunshine et al. | |
| 6,196,051 B1 * | 3/2001 | Marshall et al. | 73/23.34 |
| 6,448,695 B2 | 9/2002 | Milsom | |
| 6,467,332 B1 | 10/2002 | Bertschi et al. | |

(Continued)

FOREIGN PATENT DOCUMENTS

| | | |
|---|---|---|
| EP | 0 822 579 A1 | 2/1998 |
| EP | 1 324 382 A1 | 7/2003 |

(Continued)

OTHER PUBLICATIONS

Benetti, M. et al., "Chemical Sensor Based on Thin Film Bulk Acoustic Wave Resonator (TFBAR)," Proceedings of the 10th Italian Conference on Sensors and Microsystems, Firenze, Italy, pp. 326-331, Feb. 15-17, 2005.

(Continued)

*Primary Examiner* — Lisa Caputo
*Assistant Examiner* — Punam Roy
(74) *Attorney, Agent, or Firm* — Seed IP Law Group PLLC

(57) ABSTRACT

A cartridge-like chemical sensor is formed by a housing having a base and a cover fixed to the base and provided with an input opening, an output hole and a channel for a gas to be analyzed. The channel extends in the cover between the input opening and the output hole and faces a printed circuit board carrying an integrated circuit having a sensitive region open toward the channel and of a material capable to bind with target chemicals in the gas to be analyzed. A fan is arranged in the housing, downstream of the integrated device, for sucking the gas after being analyzed, and is part of a thermal control system for the integrated circuit.

22 Claims, 7 Drawing Sheets

U.S. PATENT DOCUMENTS

| | | | |
|---|---|---|---|
| 6,883,364 B2 * | 4/2005 | Sunshine et al. | 73/23.34 |
| 6,933,807 B2 | 8/2005 | Marksteiner et al. | |
| 7,071,073 B2 | 7/2006 | Villa et al. | |
| 7,294,536 B2 | 11/2007 | Villa et al. | |
| 2003/0062807 A1 | 4/2003 | Takeuchi et al. | |
| 2004/0055363 A1 * | 3/2004 | Bristol | 73/31.03 |
| 2004/0132059 A1 * | 7/2004 | Scurati et al. | 435/6 |
| 2004/0172798 A1 | 9/2004 | Ruby et al. | |
| 2005/0208696 A1 | 9/2005 | Villa et al. | |
| 2005/0233440 A1 * | 10/2005 | Scurati et al. | 435/287.2 |
| 2006/0019273 A1 | 1/2006 | Connolly et al. | |
| 2006/0125489 A1 | 6/2006 | Feucht et al. | |
| 2006/0216812 A1 | 9/2006 | Okada et al. | |
| 2006/0257286 A1 | 11/2006 | Adams | |
| 2010/0107739 A1 | 5/2010 | Marra | |
| 2010/0163410 A1 | 7/2010 | Mastromatteo et al. | |
| 2010/0170324 A1 | 7/2010 | Mastromatteo et al. | |
| 2011/0318840 A1 | 12/2011 | Ziglioli et al. | |
| 2012/0168882 A1 | 7/2012 | Cherian et al. | |
| 2012/0171713 A1 | 7/2012 | Cherian et al. | |
| 2012/0171774 A1 | 7/2012 | Cherian et al. | |
| 2012/0286381 A1 * | 11/2012 | Ziglioli | 257/415 |

FOREIGN PATENT DOCUMENTS

| | | |
|---|---|---|
| EP | 1 403 383 A1 | 3/2004 |
| EP | 1 246 699 B1 | 1/2007 |
| IT | RM2001A000455 | 7/2001 |
| WO | 01/54813 A2 | 8/2001 |

OTHER PUBLICATIONS

Matsumoto, H. et al., "Influence of Underlayer Materials on Preferred Orientations of Sputter-Deposited AlN/Mo Bilayers for Film Bulk Acoustic Wave Resonators," *Japanese Journal of Applied Physics* 43(12):8219-8222, 2004.

Rosenbaum, J. F., "Bulk Acoustic Wave Theory and Devices," Boston, MA: Artech House, 1988, 7 pages.

Hwang et al., "CMOS VLSI Potentiostat for Portable Environmental Sensing Applications," *IEEE Sensors Journal* 10(4):820-821, Apr. 2010.

Richter et al., "A High Performance Silicon Micropump for Fuel Handling in DMFC Systems," proceedings of the Fuel Cell Seminar, Miami Beach, FL, USA, pp. 272-275, Nov. 3-7, 2003.

Schienle et al., "A Fully Electronic DNA Sensor With 128 Positions and In-Pixel A/D Conversion," *IEEE Journal of Solid-State Circuits* 39(12):2438-2445, Dec. 2004.

Turner et al., "A CMOS Potentiostat for Amperometric Chemical Sensors," *IEEE Journal of Solid-State Circuits*, SC-22(3):473-478, Jun. 1987.

Yang et al., "Amperometric Electrochemical Microsystem for a Miniaturized Protein Biosensor Array," *IEEE Transactions on Biomedical Circuits and Systems* 3(3):160-168, Jun. 2009.

Zhang et al., "Electrochemical Array Microsystem with Integrated Potentiostat," *IEEE Sensors*, pp. 385-388, 2005.

* cited by examiner

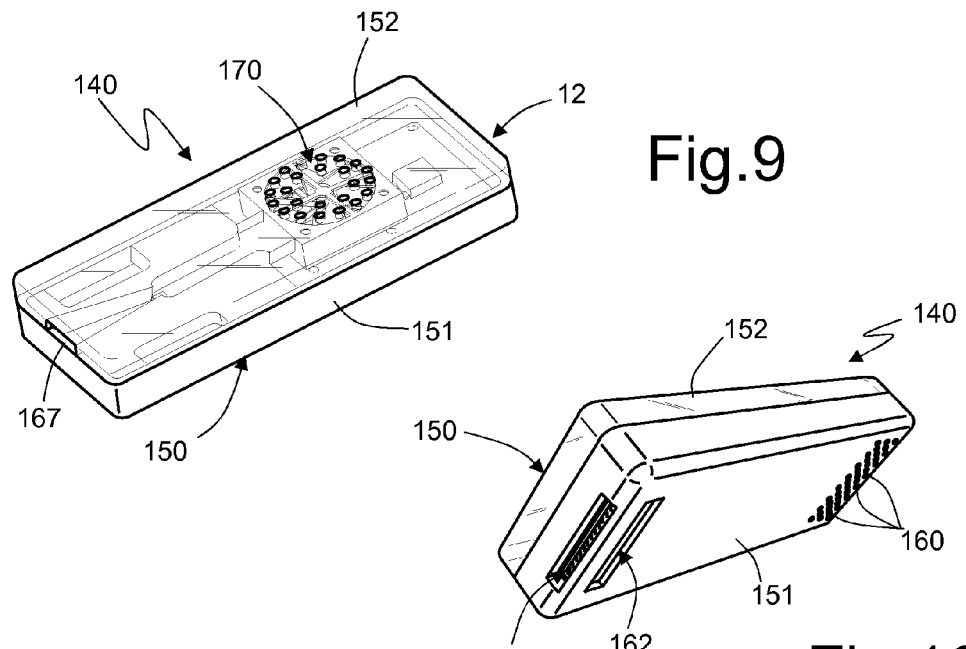
Fig. 9
Fig. 10
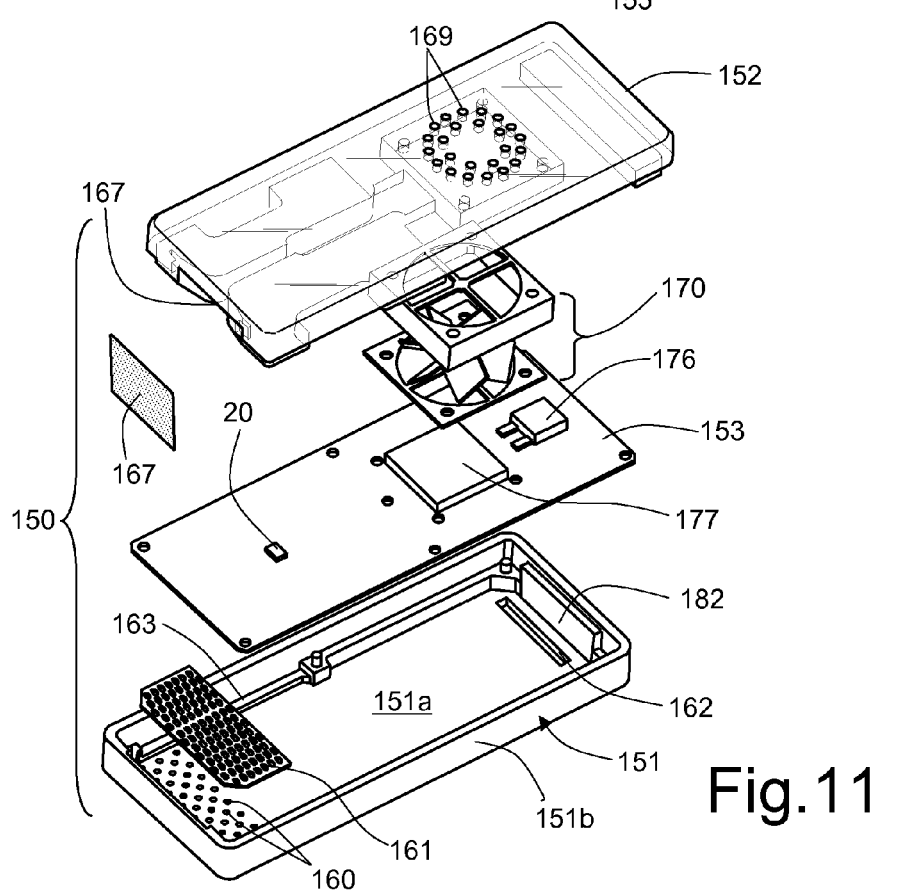
Fig. 11

INTEGRATED CHEMICAL SENSOR FOR DETECTING ODOROUS MATTERS

BACKGROUND

1. Technical Field

The present disclosure relates to an integrated chemical sensor for detecting odorous matters.

2. Description of the Related Art

As is known, the request for microsensors of small dimensions has led to the study of integrated solutions that apply the techniques and know-how acquired in the manufacture of semiconductors. In particular, integrated sensors using piezoelectric layers for detecting acoustic waves have been studied, wherein a piezoelectric material layer, arranged between two electrode layers, overlies a cavity and forms an acoustic resonator (see, for example, "Bulk Acoustic Wave Theory and Devices" Joel F. Rosenbaum Artech House Inc., 1988).

These electro-acoustic resonators have been proposed for manufacturing sensors of different types, such as force, pressure, acceleration, weight, and chemicals detecting sensors, which exploit the variation of the oscillating frequency of the acoustic resonator following a variation of its mass and/or of its geometrical configuration. In practice, the resonator forms an integrated microbalance based upon the piezoelectric effect.

Recently, the use of microbalances as chemical sensors (electronic noses) has caused particular interest. These sensors find in fact application in the foodstuff sector, where they can be used for controlling the freshness of foodstuffs in the fishery industry (fish, mollusks, etc.), for assessing the seasoning of cheese, for controlling the suitability of packaging, for controlling cooking of foodstuffs, for assessing the quality of beer, liqueurs and spirits. Integrated chemical sensors can moreover be used also in the cosmetics and pharmaceutical industry for controlling perfumes and aromas. The sector of environmental monitoring, the bio-medical sector and food control sector represent, instead, emerging markets for electronic noses. In all these fields they can be used for detecting chemical species produced by bacteria, for example, in environmental applications, for detecting cyanobacteria in lakes and rivers, in the medical field for detecting the presence of *Escherichia coli* and in food production field by identifying molecules produced by microorganisms formed in production processes. Finally, a market that represents an economically very promising outlet for electronic noses or, more in general, for automatic gas-detection systems is represented by the automotive sector. In this field, manufacturers are interested in controlling the quality of the air in the passenger compartment of vehicles and in controlling the exhaust gases.

For an application as an electronic nose, an apparatus has been proposed that comprises a plurality of quartz chemical sensors, each formed by a quartz region having a surface covered by an adsorbent layer, which is able to bind in a non-selective way with the volatile substances in the environment (ITRM2001A000455). In practice, the quartz forms, with an associated oscillating circuit, an electrical resonator having a natural resonance frequency comprised between 1 MHz and 1 GHz. Each sensor is provided with a different adsorbent layer. When the chemicals in the environment (analytes) are adsorbed by one or more chemical sensors, the latter increase in weight, varying their own masses, and thus their own resonance frequency. Alternatively, the relaxation time of the oscillations is measured.

An electronic processing circuit connected to the chemical sensors processes the generated signals and compares them with known configurations in order to recognize the chemicals.

Known quartz sensors may, however, be improved, in particular as regards sensitivity and the overall dimensions, which do not enable use thereof in many applications. The use of quartz renders moreover production complex and burdensome.

Sensors formed on silicon substrates have moreover been proposed, having cavities obtained by "bulk micromachining" using tetramethyl-ammonium hydroxide (TMAH, see for example "Sensors and Microsystems: Proceedings of the 10th Italian Conference" A. G. Mignani, R. Falciai, C. Di Natale, A. D'Amico, World Scientific Publishing Company, July 2008). This solution comprises depositing, on a surface of a silicon wafer, a silicon nitride layer, operating as an etch stop, a first aluminum layer (bottom electrode), an aluminum nitride layer (piezoelectric material), and a second aluminum layer (second electrode). Then, an anisotropic back etching is performed, which stops on the silicon nitride layer, and the wafer is singled (using a process usually called "dicing"). In each die thus obtained, the stack of layers on the front defines a diaphragm, whereon a thin layer of a sensitive material, such as porphyrin, is deposited.

In this process, the machining is costly and the use of TMAH is not usual in present production lines for integrated circuits.

In addition, the etching procedure causes the formation, in the substrate, of a cavity having a trapezoidal cross-section having a minor base formed by the diaphragm and sides inclined by 45°-50°. Since the thickness of the substrate is generally 675-700 µm, the major base of the cavity occupies an area having a side or diameter of 1.2-1.4 mm added to the width of the diaphragm. The minimum total area required by each microbalance is thus much greater than that due to the oscillating region alone. The microbalance thus has large overall dimensions, which reduces the possibility of integration thereof.

Consequently, in general, known sensors do not provide the desired sensitivity, involve complex manufacturing processes, present high costs and dimensions such as not to enable a wide application thereof.

Italian patent application TO2008A001012 discloses the structure of an integrated microbalance cell and the possibility of integrating more cells in a same integrated chip so as to form a chemical sensor having reduced dimensions and high sensitivity.

BRIEF SUMMARY

One embodiment of the present disclosure is a cartridge-like chemical sensor structure that exploits the potentiality of the microbalance cell of the above mentioned Italian patent application, in particular that has low costs and very limited bulk so as to be usable in a broad range of applications.

According to the present disclosure there are provided an integrated chemical sensor and the manufacturing process thereof.

BRIEF DESCRIPTION OF THE SEVERAL VIEWS OF THE DRAWINGS

For a better understanding of the present disclosure, a preferred embodiment thereof is now described, purely by way of non-limiting example, with reference to the attached drawings, wherein:

FIG. 9 is a top perspective view of the present sensor;

FIG. 10 is a bottom perspective view of the sensor of FIG. 9;

FIG. 11 is an exploded view of the sensor of FIG. 9;

DETAILED DESCRIPTION

Figure 3:
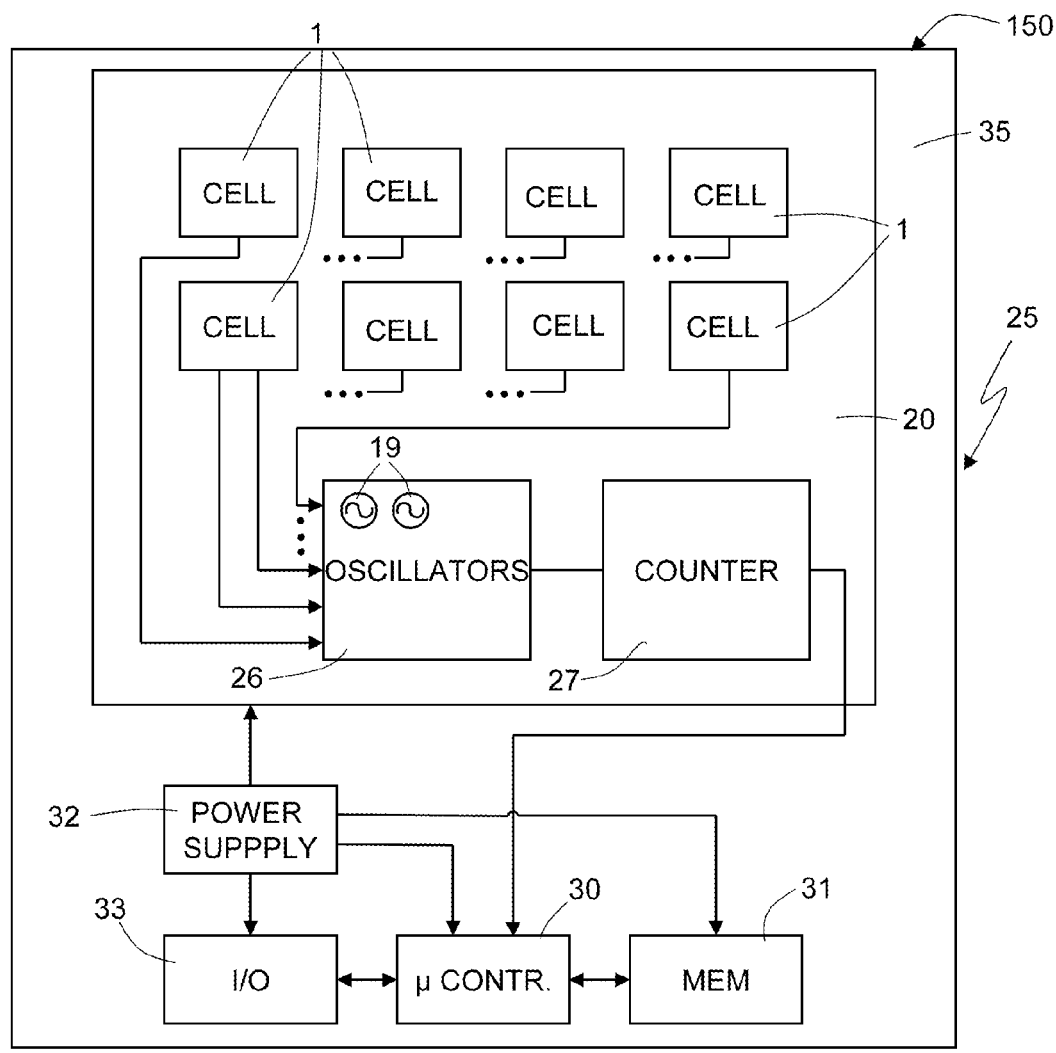
FIG. 3 is a block diagram of an apparatus for detecting chemical substances including the sensor of FIG. 2.

A chemical sensor according to one embodiment comprises a plurality of microbalance cells 1 that are integrated in a semiconductor material chip 20 as shown in FIG. 3. For example, each microbalance cell 1 may be formed using any of the cells 1A-1E shown in FIGS. 1 and 4-7.

Figure 1:
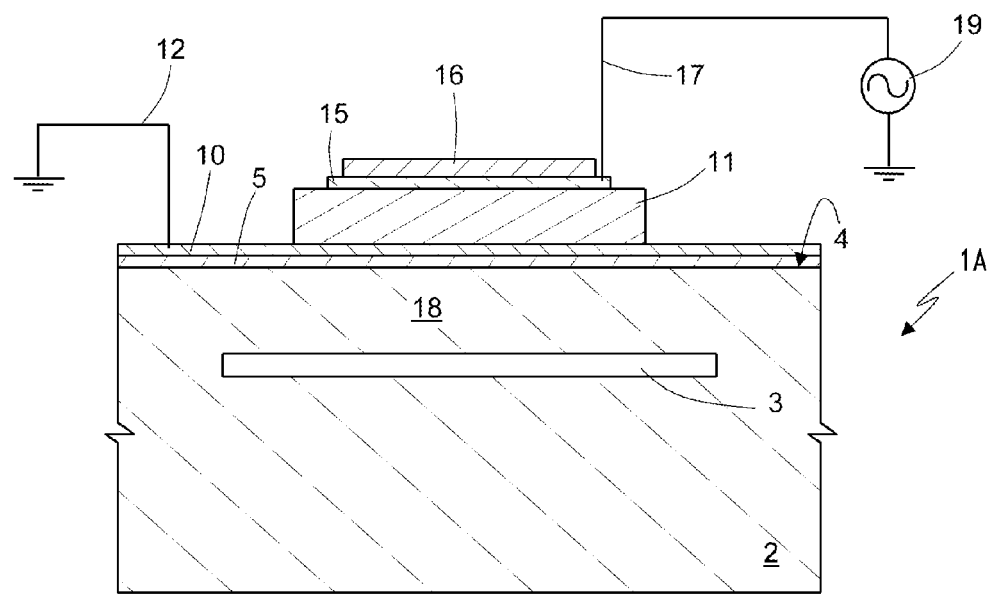
FIG. 1 is a cross-section of a silicon wafer integrating an electronic microbalance cell.

FIG. 1 shows a cell 1A disclosed in Italian patent application TO2008A001012. Cell 1A is integrated in a body 2 of semiconductor material, for example, monocrystalline silicon, having a surface 4 and a buried cavity 3, which delimits a bottom side of a diaphragm 18, also of monocrystalline silicon.

A buffer layer 5, for example of aluminum nitride (AlN), extends above the diaphragm 18, and a bottom electrode 10, for example of molybdenum, extends on the buffer layer 5. Here, the buffer layer 5 has a thickness comprised between 30 and 100 nm, for example 50 nm, and the bottom electrode 10 has a thickness of 50-150 nm, for example 100 nm.

A piezoelectric region 11 extends on the bottom electrode 10 and has here a smaller area than the electrode 10 so as to enable electrical connection of the bottom electrode 10, as represented by wire 12, to a ground potential. The piezoelectric region 11 has a thickness of 1-3 µm, for example, approximately 2 µm.

A top electrode 15, which is, for example also of molybdenum and has a thickness of 50-150 nm, for example 100 nm, extends on the piezoelectric region 11. The top electrode 15 can have same area as, or a smaller area than, the piezoelectric region 11 and is connected, for example via a wire 17, to an oscillator 19, of a known type and not shown in detail.

A sensitive region 16 extends on the top electrode 15. The sensitive region 16 is of a material such as to bind with the chemical to be detected, in particular, a metal-porphyrin having affinity with this chemical. Finally, a passivation layer (not shown) may be deposited and opened to form contacts (not shown).

Operation of the cell 1 of FIG. 1 is the following. The circuit formed by the piezoelectric region 11 and by the oscillator 19 forms an electrical resonator having a natural oscillation frequency. When a mass is deposited on the sensitive region 16 or an analyte binds thereto, the resonator undergoes a variation of the oscillating frequency Δf according to the Sauerbray equation:

$$\Delta f = -\frac{2f_o^2}{A\sqrt{\mu\rho}}\Delta m \quad (1)$$

where Δm is the mass variation due to the added mass, $f_o$ is the natural oscillation frequency of the resonator, µ is the shear modulus, ρ is the density, and A is the area of the oscillating surface (area of the base of the parallelepiped or in general of the solid formed by the piezoelectric region 11). Thus, by measuring frequency variations, it is possible to understand whether target chemicals have been adsorbed, selectively bound to the sensitive region(s) 14. From the mass variation, it is also possible to detect the quantity of adsorbed substances.

Cell 1A of FIG. 1 can be made using the technique described in EP-A-1 324 382, for manufacturing an SOI wafer, and the process described in U.S. Application Publication No. 2005/0208696, for manufacturing a pressure sensor, as described in detail in above mentioned Italian Patent application TO2008A001012.

Figure 2:
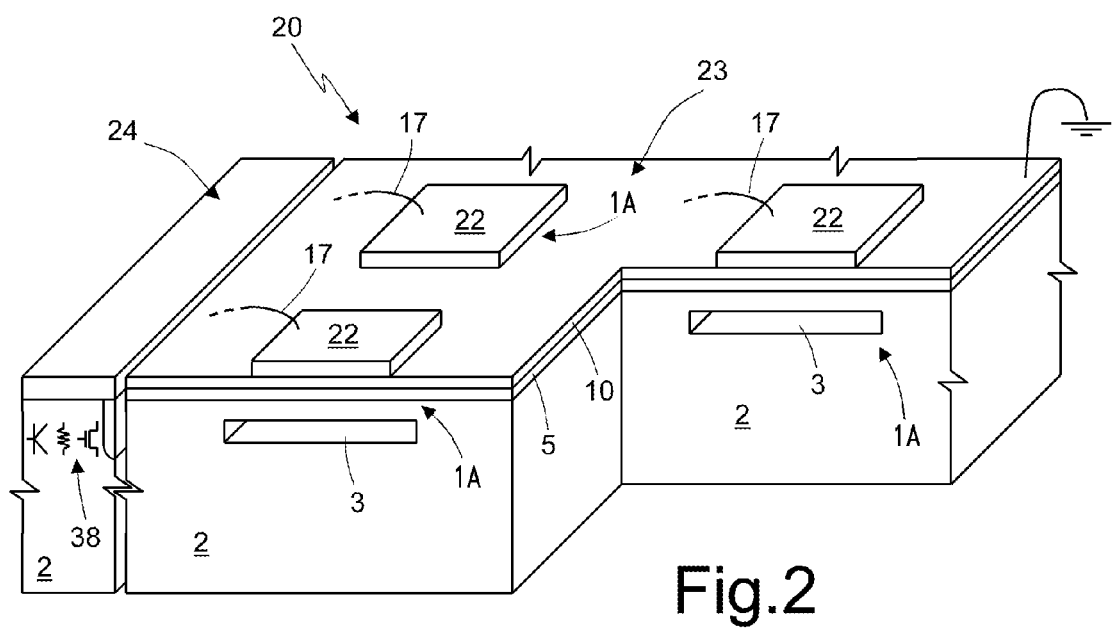
FIG. 2 is a partially sectioned perspective view of a chip integrating a plurality of cells of FIG. 1.

FIG. 2 shows a chip 20 of silicon, having a sensor portion 23 and a circuitry portion 24. Sensor portion 23 integrates a plurality of cells 1A, for example eight (only three whereof are visible), sensible to the same one or to different chemicals; circuitry portion 24 integrates electronic components of an electronic circuit 38 associated with the sensor portion 20. In FIG. 2, the cells 1A are represented schematically, with a surface region 22 representing the set of the regions 11, 15 and 16. Furthermore, the bottom electrode 10 covers the whole surface shown of the area of the cells 1A, and the wires 17 are connected to appropriate external areas. Alternatively, the bottom electrode layer 10 can be defined so as to form contact pads and interconnection lines to the associated circuitry 38.

In practice, the cells 1A are arranged in an array and the different signals generated can then be used and compared with known distributions for recognition of chemicals.

FIG. 3 shows, for example, an apparatus for recognition of odors or "electronic nose" 25 comprising a circuit board 35, carrying the chip 20, which integrates an array of eight cells 1, and the electronics 38, which includes an oscillator stage 26, including a plurality of oscillators 19, one for each cell 1, and a converter 27, for example a counter. The oscillator stage 26 drives the array of cells 1 and generates a plurality of periodic electric signals (pulse trains) having a frequency equal to the frequency f of the resonators. The counter 27 counts the number N of pulses within a fixed time interval T and generates digital signals that encode their oscillation frequencies f, the value whereof depends upon the possible bond with respective analytes bound thereto.

The output of the chip 20 is connected to a microcontroller 30 connected to a memory 31, for example, of an EEPROM type, to a power-supply stage 32 and to an input/output stage 33, for example for displaying the results. The microcontroller 30 is thus able to detect any frequency difference Δf for each cell 1 and, according to patterns stored in the memory 31, to recognize the chemicals present in the environment.

The odor-recognition apparatus 25 is accommodated in a housing 150, as described hereinafter.

Figure 4:
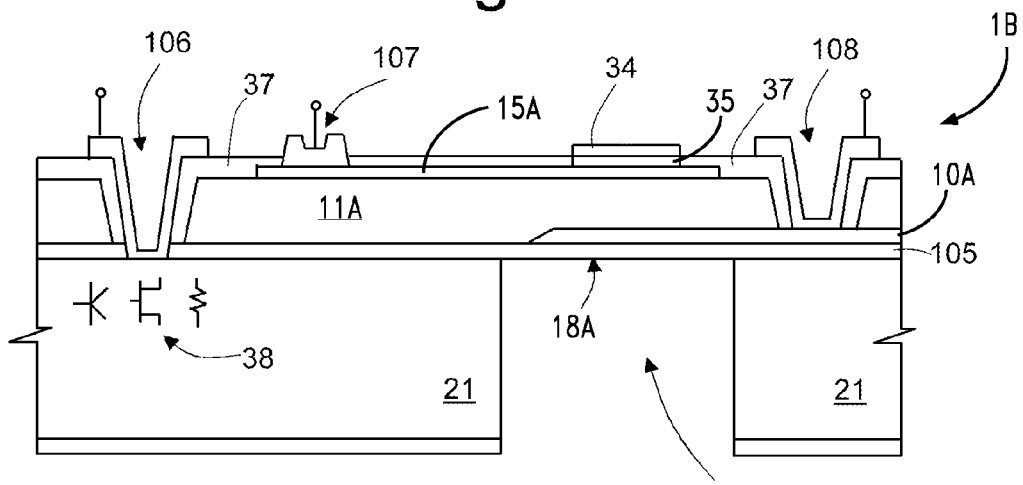
FIGS. 4-7 show different embodiments of the cell of FIG. 1.

FIG. 4 shows a cell 1B wherein the cavity underlying the diaphragm is not buried. Here, a substrate 21 has a trench 100 obtained using the technique of bulk micromachining by selectively removing a portion of the silicon substrate 21 from the back using a reactive ion etching plasma tool. A dielectric layer 105, e.g., thermally grown silicon dioxide, extends on the surface of the substrate 21 and defines a diaphragm 18A.

A protection or passivation layer 37, e.g., of SiN, extends on the surface of the cell 1A, except at the sensitive region 34 and at contacts 106-108.

Here, a bottom electrode 10B protrudes with respect to the piezoelectric region 11B, to allow electrical connection of bottom electrode 10B to ground through a contact 108. A bond region 35, e.g. of NiPdAu, extends between the upper electrode 15B and the sensitive region 34.

Figure 5:
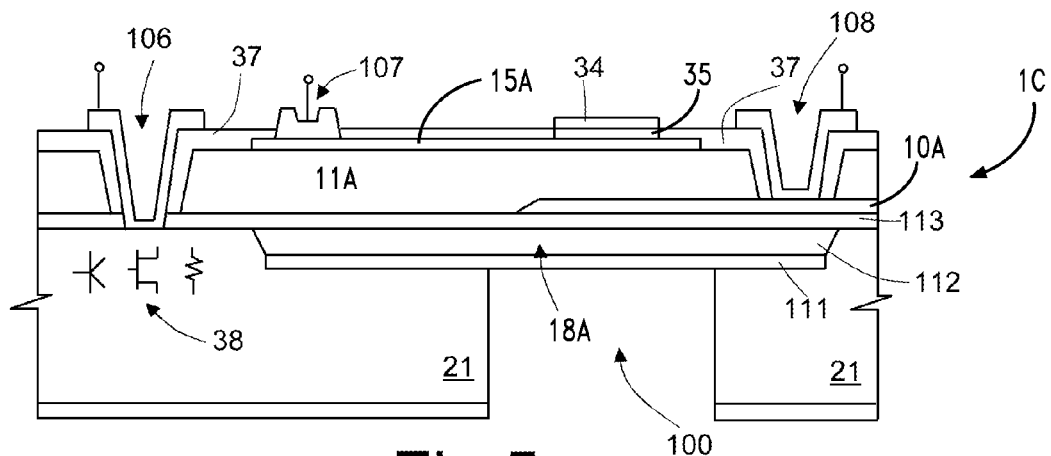

In FIG. 5, a cell 1C includes a diaphragm 18A formed by a multilayer including a bottom dielectric region 111 (e.g., of silicon dioxide), a polysilicon portion 112 and an upper dielectric layer 113 (e.g., of silicon dioxide). Such a structure may be obtained, by interrupting the epitaxial growth, forming bottom dielectric region 111 (using a selective thermal growth or a deposition), and prosecuting the epitaxial growth, so that the polysilicon portion 112 is formed only on the bottom dielectric region 111.

Figure 6:
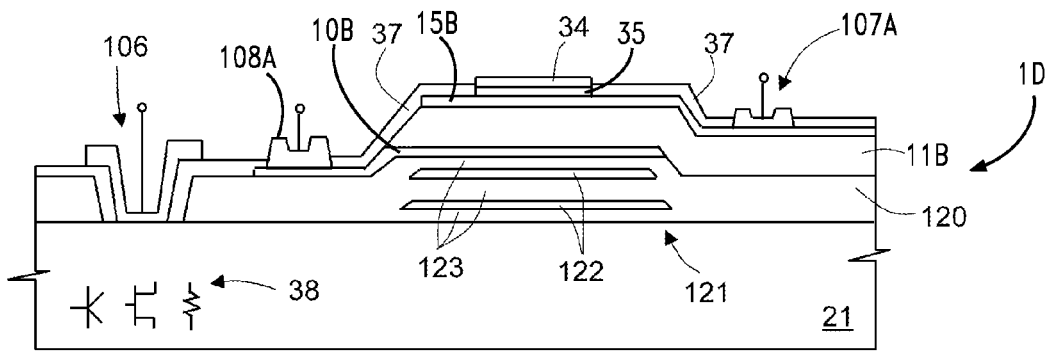

FIG. 6 shows a cell 1D using a Bragg mirror to contain the acoustic waves in the overlying piezoelectric region 27 and thus is functionally equivalent to the buried cavity 3 or the trench 100. In detail, here, the substrate 21 is covered by a thick dielectric layer 120 which accommodates a mirror 121 for each cell 1D. The mirror 121 is formed by a stack of alternating high acoustic impedance layers 122 and low acoustic impedance layers 123 as described, e.g., in U.S. Pat. No. 6,448,695 or U.S. Pat. No. 6,933,807.

Also in FIG. 6, a bottom electrode 10B extends on the mirror 121 and extends beyond a piezoelectric layer 11B to a bottom contact 108A. A top electrode extends between the piezoelectric layer 11B and the bond region 35 and extends laterally to contact an electrical contact 107A.

Figure 7:
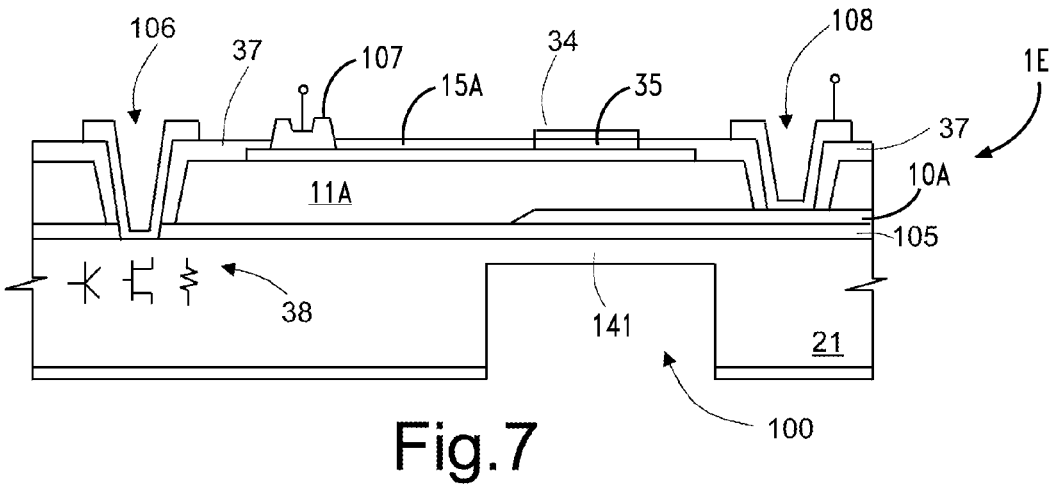

FIG. 7 shows a cell 1E wherein the cavity 100 does not extend through the substrate 21. This solution may be obtained using a technique different from bulk micromachining, e.g., using the process described in U.S. Pat. No. 7,294,536 or in U.S. Pat. No. 7,071,073, by forming a buried oxide layer, removing the silicon of the substrate 21 from the back until reaching the buried oxide layer (for example, through plasma reactive ion etching) and removing the buried oxide layer, thereby forming a diaphragm 141.

Figure 8:
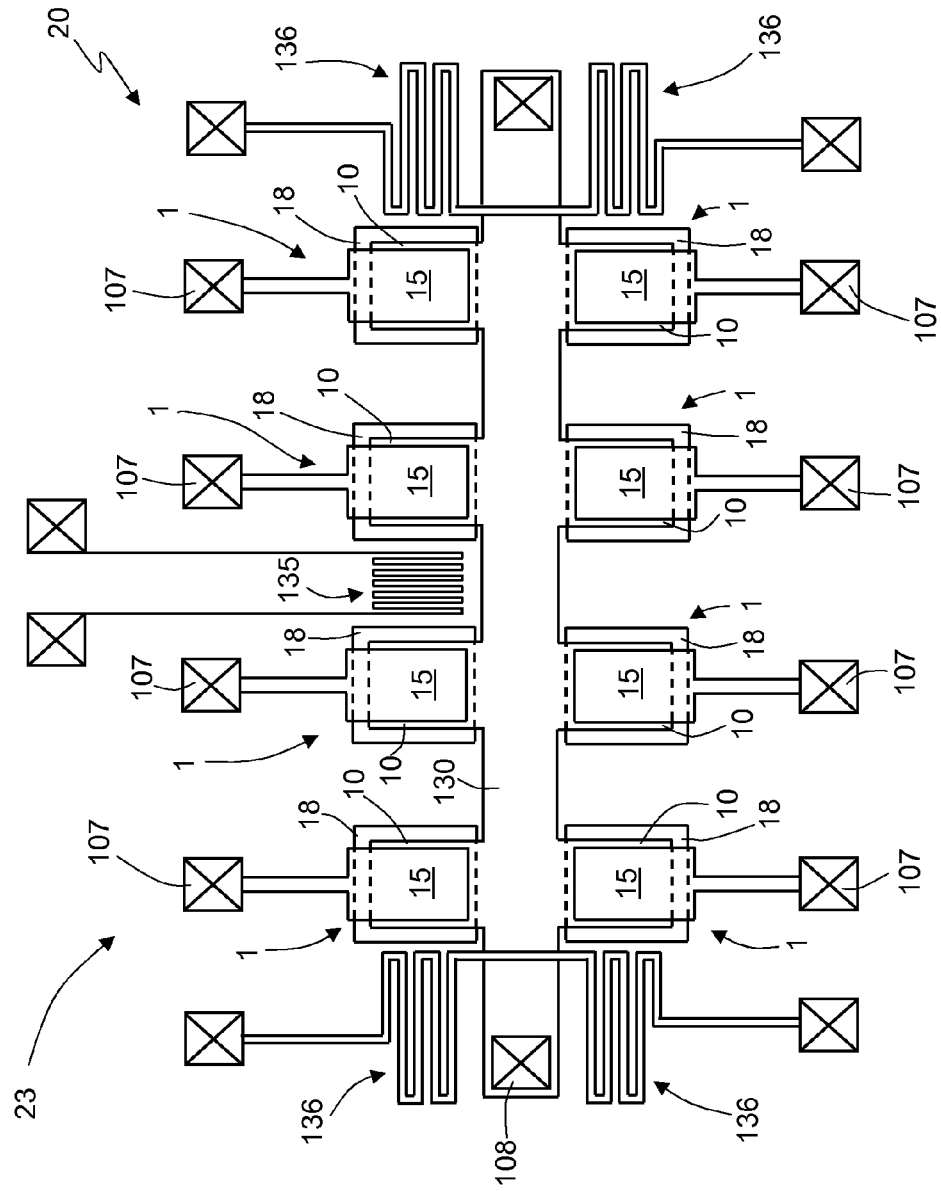
FIG. 8 is a top view of the cell layout in the chip of FIG. 2.
Figure 12:
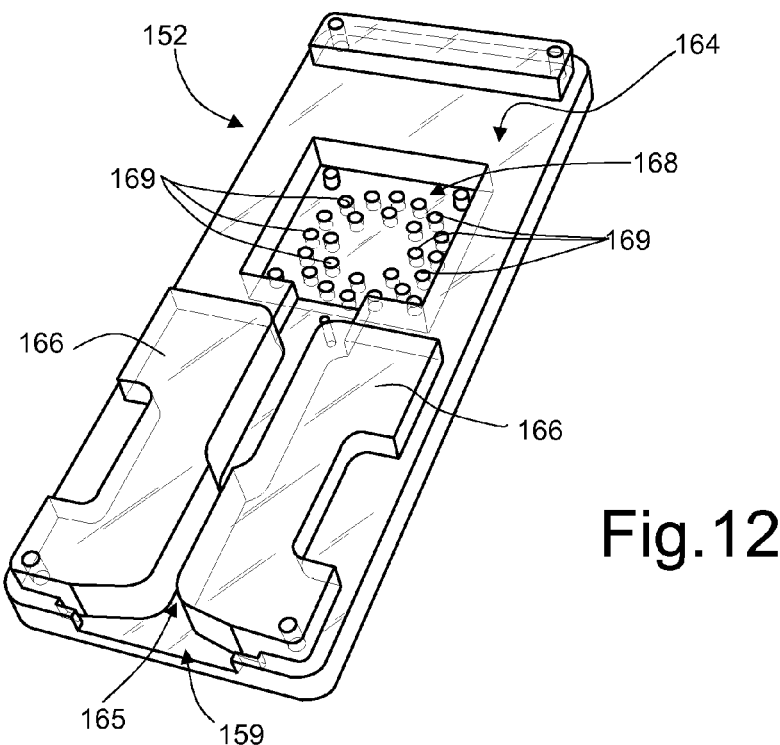
FIG. 12 is a bottom view of a cover of the sensor of FIG. 9.

FIG. 8 is a top view of the sensor portion 23 of a chip integrating a plurality of cells 1, made according to any of FIGS. 1, 4-7.

In FIG. 8, an integrated heater 135 is formed using the aluminum metallization that forms the contacts of the cells 1. Here, each cell 1 has an own top electrode 15 connected to an own contact 107 and overlying an own diaphragm 18, each defined by an underlying cavity 3 or trench 100 or Bragg mirror 121. The bottom electrodes 10 of cells 1 are connected together through a connecting line 130 connected to contacts 108. At least one heater 135 is formed in the sensor portion 23, e.g., in a central area thereof. The heater 135 is for example formed of an aluminum coil, in the same metal level as contacts 107-108. Moreover, temperature sensors 136 are formed laterally to the sensor portion 23. They may also be formed of aluminum, in the same metal level as the contact 107-108 and the heater 135. Thereby, forming the heater 135 and the temperature sensors 136 does not require additional masks.

FIGS. 9-14 show a chemical sensor 140 formed as a handheld cartridge and including the chip 20 for performing measures of chemicals in the environment and/or of gas inserted in the cartridge.

In detail, the chemical sensor 140 as shown comprises a housing 150 shaped so as to guide the gas to be analyzed toward the chip 20 and to actively intervene in controlling the temperature of the sensor portion 23; a circuit board 153, accommodated in the housing 150 and supporting the chip 20 (integrating cells 1 and electronics 38, including the oscillators 26 and the counter 27) and other operative circuits, as described hereinbelow; and a connector port 182 (FIG. 15), formed on the housing 150 to allow data connection with the outside.

Housing 150 comprises a base 151 and a cover 152 and has a generally parallelepipedal shape, defining a longitudinal direction along which gas to be analyzed and cooling air flow, as explained in more detail later on. In one embodiment, the housing 150 has pocket dimensions, with a longer side (length) of at most 15 cm; for example, housing 150 can have a length of 50-100 mm, a width of 30-40 mm and a height of 10-17 mm.

The base 151, e.g., of aluminum or polymer, has a shell-like shape including a bottom surface 151a and a raised edge 151b. The bottom surface 151a, near a first longitudinal end thereof, has a plurality of input openings 160 covered by a filter 161, e.g., of metal, carbon fibers or spun polymer. An exit opening 162 may be arranged on the opposite longitudinal end of the base 151 and spacers 163 are formed in the base 151 for peripherally supporting the board 153 at about half of the height of the base 151. Thereby, a cooling chamber 154 is formed between the base 151 and the board 153 and is connected to the exterior through the input openings 160 and the exit opening 162.

The cover 152 is of plastic, e.g., polycarbonate or other polymer compatible with confining odorous molecules, and closes upwardly the base 151 and has a non-uniform thickness. In detail, FIG. 12, an internal face 164 of the cover 152 defines a reference plane intended to abut against the raised edge 151b of the base 151. Projecting portions 166 extend from the internal face 164 into the base 151 and centrally delimit a test portion 165A of a channel 165 extending along the cover 152 in longitudinal direction, from an input opening 159 of the cover 152 until a central portion thereof. Here, the channel 165 opens onto a recess 168, where the cover 152 has reduced thickness, and is crossed by air holes 169, which connect recess 168 to the exterior of the housing 150.

An input air filter 167 is arranged near the input opening 159, at the input end of the channel 165, and a fan 170 is fixed to the housing 150, in the recess 168.

The bottom face of the cover 152, in particular the surface of the channel 165, may be covered by antistatic material or may be plated with gold or other inert metals.

Figure 13:
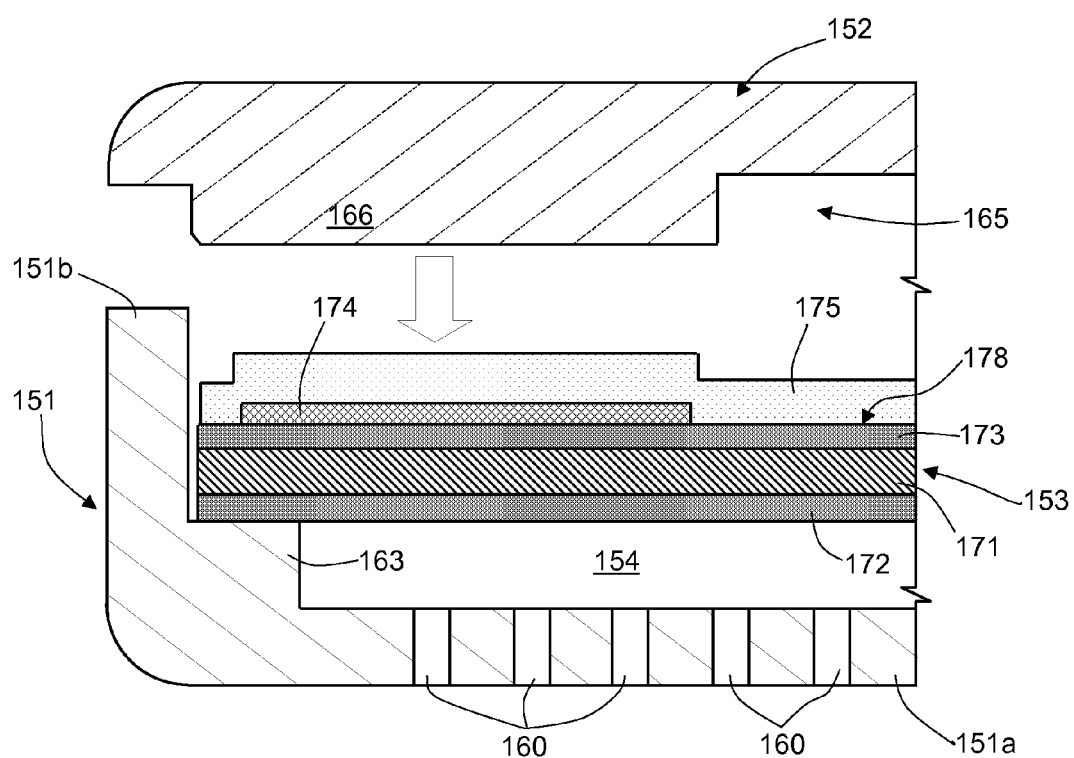
FIG. 13 is a cross-section of a detail of the sensor of FIG. 9.

The board 153 is formed for example by an organic multilayer including an organic substrate 171, e.g., of BT (bismalesimide triazine), epoxy, FR-4 (Flame Retardant 4), LCP (Liquid Crystal Polymer) or polyimide, covered on both faces by suitable electromagnetic insulating layers, e.g., by a bottom copper foil 172 and by a top copper foil 173 (FIG. 13). Shims or protrusions 174 are formed on the top copper foil 173, in front of the projecting portions 166 of the cover 151. Shims 174 can be obtained as copper platings. Moreover, a solder mask 175, with a thickness of e.g., 20-40 μm, covers the board 153, at least at the projecting portions 166, where the board 153 is in contact with the cover 152. Thereby, the board 153 has a higher thickness at the contact zones with the cover 152 and the relative dimensions are studied so as to generate a mechanical interference between the board 153 and the cover 151, at least at the sides of the channel 165. This interference ensures a lateral sealing of the channel 165, avoiding any flow rate loss within the channel 165 and allowing a control of the aspiration flow of the fan 170 and thus of the thermal behavior in the chip 20, as discussed in more detail hereinafter.

Figures 14, 15:
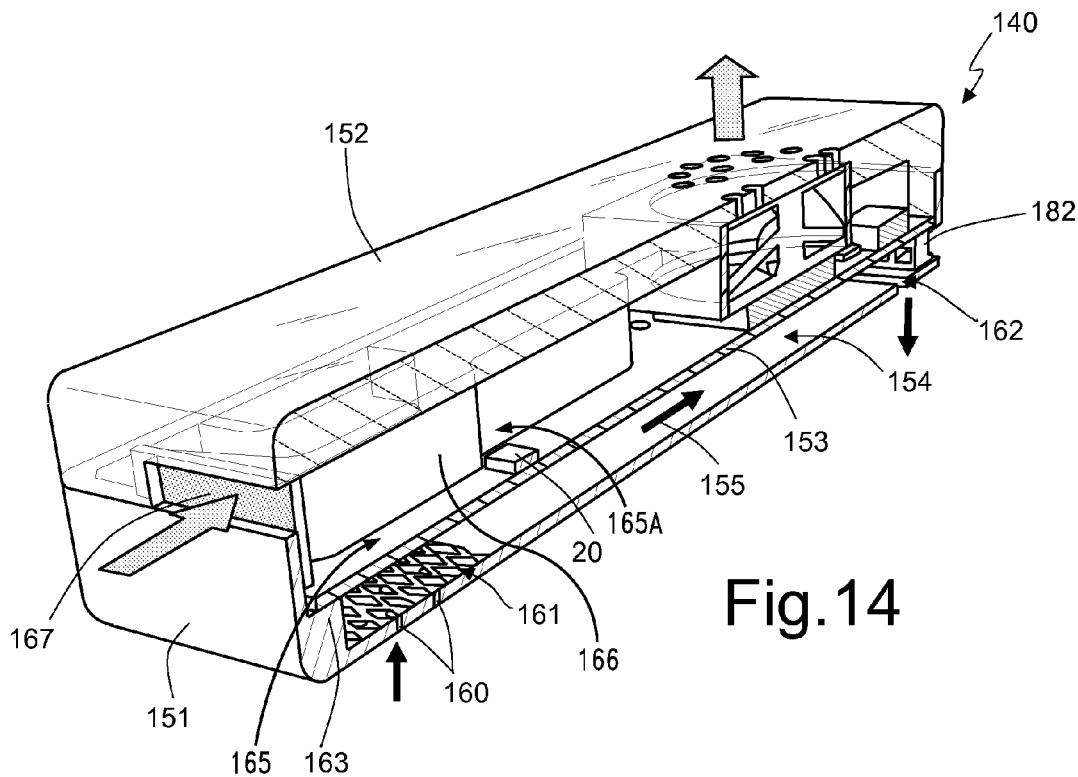
FIG. 14 is a perspective view of a longitudinal section of the present sensor.
FIG. 15 shows the connection between the sensor of FIG. 12 and a laptop.

The board 153 supports, in addition to the chip 20, a fan controller 177, connected through wires, not shown, to the fan 170, and an auxiliary chip 176, e.g., a memory controller, a signal treatment circuit or the like. In particular, the auxiliary chip 176 may store a program for managing the temperature in the chip 20, namely, in the sensor portion 23, on the basis of the temperature signals measured by the temperature sensors 136, increasing or reducing the current supplied to the heater 135 and the rotation speed of the fan 170, through the fan controller 177 that feeds the fan 170 with a d.c. current that is proportional to the target rotation speed. As an alternative, the fan can be controlled through an external computer (FIG. 15).

In a way not shown, the input opening 159 may be connected to an external duct that physically connects the channel 165, and thus the chip 20, with an external volume containing odorous molecules to be analyzed.

The dimensions and shape of the cooling chamber 154, as well as the relative arrangement of the fan 170, may be optimized so as to obtain a laminar air flow on the chip 20 and thus an efficient cooling thereof, when desired. For example laminar flow conditions have been obtained with a channel 165 having a overall length of 25-50 mm, with an initial portion near the input aperture 159 (with a length of e.g., 1-25 mm) having a reduced width of, e.g., 2-6 mm, and a final portion near the recess 168 having a larger width, e.g., 6-10 mm.

The cooling chamber 154 makes cooling and dissipation of the heat generated in the chip 20 easier, in particular if the base 151 is made of aluminum. Moreover, air vents (not shown) may be provided in the board 153, next to the fan 170, so as to generate a vacuum in the cooling chamber 154. Thereby, the cooling chamber 154 is flown by an air stream that contributes to remove heat generated during the operation, as shown schematically in FIG. 14 by the arrow 155.

The chip 20, the fan controller 177 and any auxiliary chips are assembled according to the chip-on-board technique and the bonding wires are covered by a "glob top".

In the chemical sensor 140, as visible from FIG. 14, the fan 170 is arranged downstream of the channel 165 and operates to suck the gas to be analyzed into the housing 150 through the input air filter so that the gas flows first on the chip 20 and then to the fan 170. Consequently, any polluting material or any particles emitted by the fan 170 cannot contaminate the gas being analyzed in the chip 20.

According to FIG. 15, the chemical sensor 140 may be connected to a personal computer 180 through an interface 181 connected to the connectors 182 supplying the data from the chip 20.

The realization of the chemical sensor 140 as a hand-held cartridge, with the heater 135 and the temperature sensors 136 integrated next to the sensitive regions 16, the presence of a gas flow control system obtained through the conformation of the housing itself and the arrangement of the fan 170 within the housing, the arrangement of the cooling chamber 154 and the present of the fan controller 177 cooperate to obtain a very effective control temperature system controlling the temperature of the sensor portion 23 of the chip 20 and a modulation of the sensitivity of the chemical sensor 140.

In particular, it is possible to modify the flow of gases on the chip 20 as a function of the measure to be carried out and the concentration of the analyte in the input air. In fact, by increasing the rotation speed of the fan 170, it is possible to increase the gas flow on the chip 20 and thus the sensitivity of the chemical sensor 140. Furthermore, by varying the speed of the fan 170 it is possible to modify the cooling effect on the chip 20; higher ventilation levels allow to increase cooling while with lower ventilation levels heating caused by the heater 135 becomes predominant. The presence of temperature sensors 136 allows a precise control of the temperature in the chip 20, according to the desired action.

In addition, the temperature control system implemented by the heater 135, the temperature sensors 136, the fan 170 and the cooling chamber 154 allow the chemical sensor 140 to be cleaned simply and quickly, after every olfactory operation.

In fact, after each olfactory operation, the cells 1 are to be brought back to the starting conditions, by cleaning the chemically active materials, e.g., the metal-porphyrins, of the sensitive regions 16. This operation is generally performed by causing dry air to flow on the chemically active materials. Here, a controlled air stream is sucked in the channel 165 and heated at a suitable temperature. Thereby, the "desorption" process and thus releasing of the substances adsorbed by the sensitive region 16 during the previous olfactory operation is helped. The control of the cleaning and then calibration air stream occurs thus in a coordinated manner with the temperature control through the heater 135 and the temperature sensors 136, so as to ensure resetting of the initial conditions and a correct execution of subsequent olfactory operations.

Thereby, the costly Peltier cell can be eliminated, reducing dimensions, weight and cost of the sensor.

The housing 150 is thus an active component of the chemical sensor 140 and moreover allows a filtering operation on the gas to be analyzed, in particular for supplying the chip 20 only with the particulate that is to be analyzed. For example, according to the input air filter 167, it is possible to analyze particulate PM1, that is particulate having an average aerodynamic diameter lower than 1 µm, or particulate PM10, that is particulate having an average aerodynamic diameter lower than 10 µm.

The integrated chemical sensor 140 has the following advantages:
- the system is closed, but the input gas stream is controlled by the fan 170 at adjustable speed;
- the sensitivity of the chemical sensor 140 may be modulated through the rotation speed of fan 170 (in a first approximation, an increase in the speed causes an increase of the stream and thus of the probability that the substances to be detected are captured by the sensitive regions 16), the time the stream is maintained on the chip 20, and the temperature of the chip;
- the input air filter 167 allows a selective filtration of the substances to be analyzed;
- the channel 165 allows the obtainment of a laminar flow on the chip 20;
- the fan 170 does not generate contaminants or extraneous particles that could go on the chip 20; any contaminant introduced by the motor of the fan are induced to get out following the gas steam downwardly to the chip 20;
- the input opening 159 can be coupled to a straw or a nozzle or directly connected to a conduit configured to receive the air flow as exhaled by a person undergoing an medical examination;
- the base 151 of aluminum acts also as a heat dissipator for the electronic circuitry;
- the temperature control system above described allows the chemical sensor 140 to be maintained to the desired temperature in the various steps so as to obtain accurate measures also in sequence;
- the control of the input gas flow allows to correlate the concentration of the captured analytes and thus to obtain also quantitative information on the percentage of the present target substances.

Finally, it is clear that modifications and variations can be made to the sensor described and illustrated herein, without thereby departing from the scope of the present disclosure.

The various embodiments described above can be combined to provide further embodiments. All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A chemical sensor, comprising:
   a housing that includes a base, a cover fixed to the base, an input opening, an output hole, and a channel for a gas to be analyzed, the channel extending between the input opening and the output hole;
   a circuit board extending interiorly of the housing;
   a integrated device fixed to the board and including a sensitive region open toward the channel and being of a material configured to bind with target chemicals in the gas to be analyzed; and
   a driving motor for advancing the gas to be analyzed, the driving motor being housed in the housing, wherein:
      the cover has internally a non-planar surface including projections extending toward the board and laterally delimiting the channel,
      the board has protrusions facing the projections of the cover, and
      the projections and protrusions are configured to generate mechanical interference between the cover and the base.

2. A chemical sensor according to claim 1, wherein the channel is formed in the cover and the driving motor is fixed to the cover downstream of the integrated device.

3. A chemical sensor according to claim 1, comprising a sealing material interlayered between the projections of the cover and the protrusions of the base.

4. A chemical sensor according to claim 1, wherein the cover has a recess arranged downstream of the channel, in communication with the output hole and housing the driving motor.

5. A chemical sensor according to claim 1, wherein the base includes a lower surface and is configured to house the board at a distance from the lower surface so as to define a cooling chamber between the board and the lower surface, the base having cooling openings in communication with the cooling chamber.

6. A chemical sensor according to claim 1, comprising a particulate filter arranged near the input opening.

7. A chemical sensor according to claim 1, wherein the driving motor comprises a fan, the chemical sensor further comprising a speed controller coupled to the fan and configured to regulate the gas flow in the housing.

8. A chemical sensor according to claim 7, wherein the integrated device comprises a heater and a temperature sensor arranged near the sensitive region, the chemical sensor further comprising a temperature control stage coupled to the heater, temperature sensor, and speed controller.

9. A chemical sensor according to claim 1, wherein the housing has a length of at most 15 cm.

10. A method, comprising:
    detecting odorous substances through a chemical sensor, the detecting including:
    feeding a gas to be analyzed to an input opening of a housing of the chemical sensor;
    generating a stream of the gas to be analyzed along a channel and on an integrated device having a sensitive region of a material configured to bind with target chemicals in the gas to be analyzed;
    driving the gas to be analyzed toward an output hole;
    heating the sensitive region with a heater adjacent to the sensitive region in the integrated device;
    measuring the temperature of the sensitive region with a temperature sensor adjacent to the sensitive region in the integrated device; and
    modifying a flow speed of the gas within the channel based on the temperature measured.

11. A method according to claim 10, comprising cleaning the sensitive region by increasing the temperature of the sensitive region and varying the flow speed of the gas within the channel.

12. A chemical sensor, comprising:
    a housing that includes an input opening, an output hole, and a channel for a gas to be analyzed, the channel extending between the input opening and the output hole, the channel having a test portion laterally defined on opposite lateral sides by internal protruding structures extending interiorly from an inner surface of the housing that defines a first one of upper and lower sides of the channel;
    a circuit board positioned interiorly of the housing and in contact with the protruding structures, the circuit board having a surface defining a second one of the upper and lower sides of the test portion of the channel;
    a integrated device fixed to the board and including a sensitive region open in the test portion of the channel and of a material configured to bind with target chemicals in the gas to be analyzed; and
    a driving motor for advancing the gas to be analyzed, the driving motor being housed in the housing and positioned between the integrated device and the output opening.

13. A chemical sensor according to claim 12, wherein the housing has a recess arranged downstream of the channel, in communication with the output hole and housing the driving motor.

14. A chemical sensor according to claim 12, wherein the housing includes a cover and a base, the channel being positioned between the cover and the circuit board.

15. A chemical sensor according to claim 14, wherein the base includes a lower surface and is configured to house the board at a distance from the lower surface so as to define a cooling chamber between the board and the lower surface, the base having cooling openings in communication with the cooling chamber.

16. A chemical sensor according to claim 12, wherein the driving motor comprises a fan, the chemical sensor further comprising a speed controller coupled to the fan and configured to regulate the gas flow in the housing.

17. A chemical sensor according to claim 16, wherein the integrated device comprises a heater and a temperature sensor arranged near the sensitive region, the chemical sensor further comprising a temperature control stage coupled to the heater, temperature sensor, speed controller.

18. A chemical sensor, comprising:
- a housing that includes a base, a cover fixed to the base, an input opening, an output hole, and a channel for a gas to be analyzed, the channel extending between the input opening and the output hole;
- a circuit board extending interiorly of the housing;
- a integrated device fixed to the board and including a sensitive region open toward the channel and being of a material configured to bind with target chemicals in the gas to be analyzed; and
- a driving motor for advancing the gas to be analyzed, the driving motor being housed in the housing, wherein the base includes a lower surface and is configured to house the board at a distance from the lower surface so as to define a cooling chamber between the board and the lower surface, the base having cooling openings in communication with the cooling chamber.

19. A chemical sensor according to claim 18, wherein the driving motor comprises a fan and the integrated device comprises a heater and a temperature sensor arranged near the sensitive region, the chemical sensor further comprising:
- a speed controller coupled to the fan and configured to regulate the gas flow in the housing; and
- a temperature control stage coupled to the heater, temperature sensor, and speed controller.

20. A chemical sensor, comprising:
- a housing that includes a base, a cover fixed to the base, an input opening, an output hole, and a channel for a gas to be analyzed, the channel extending between the input opening and the output hole;
- a circuit board extending interiorly of the housing;
- a integrated device fixed to the board and including a heater, a sensitive region open toward the channel and being of a material configured to bind with target chemicals in the gas to be analyzed, and a temperature sensor arranged near the sensitive region;
- a driving motor for advancing the gas to be analyzed, the driving motor being housed in the housing and including a fan the integrated device comprises a heater and a temperature sensor arranged near the sensitive region;
- a speed controller coupled to the fan and configured to regulate the gas flow in the housing; and
- a temperature control stage coupled to the heater, temperature sensor, and speed controller.

21. A chemical sensor according to claim 20, wherein the channel is formed in the cover and the driving motor is fixed to the cover downstream of the integrated device.

22. A method, comprising:
- detecting odorous substances through a chemical sensor, the detecting including:
- feeding a gas to be analyzed to an input opening of a housing of the chemical sensor;
- generating a stream of the gas to be analyzed along a channel and on an integrated device having a sensitive region of a material configured to bind with target chemicals in the gas to be analyzed;
- driving the gas to be analyzed toward an output hole; and
- cleaning the sensitive region by increasing the temperature of the sensitive region and varying the flow speed of the gas within the channel.

* * * * *